US012186212B2

(12) United States Patent
Hansen et al.

(10) Patent No.: US 12,186,212 B2
(45) Date of Patent: Jan. 7, 2025

(54) PROSTHETIC FOOT/ANKLE SYSTEM WITH AUTOMATIC ALIGNMENT

(71) Applicant: U.S. Government as represented by the Department of Veterans Affairs, Washington, DC (US)

(72) Inventors: Andrew Howard Hansen, Apple Valley, MN (US); Edwin Kay Iversen, Salt Lake City, UT (US); Eric Alexander Nickel, Brooklyn Park, MN (US); Gregory O. Voss, Apple Valley, MN (US); Gregory James Jacobs, Salt Lake City, UT (US); Carter J. Greene, West Valley City, UT (US); Jeffery David Christenson, West Valley City, UT (US)

(73) Assignees: Motion Control, Salt Lake City, UT (US); The United States Government As Represented by the Department Of Veterans Affairs, Washington, DC (US)

( * ) Notice: Subject to any disclaimer, the term of this patent is extended or adjusted under 35 U.S.C. 154(b) by 151 days.

(21) Appl. No.: 17/507,527

(22) Filed: Oct. 21, 2021

(65) Prior Publication Data

US 2023/0126674 A1     Apr. 27, 2023

(51) Int. Cl.
*A61F 2/66* (2006.01)
*A61F 2/74* (2006.01)
(Continued)

(52) U.S. Cl.
CPC .............. *A61F 2/76* (2013.01); *A61F 2/6607* (2013.01); *A61F 2/744* (2021.08); *A61F 2/748* (2021.08);
(Continued)

(58) Field of Classification Search
CPC .......... A61F 2/6607; A61F 2/744; A61F 2/76; A61F 2/748; A61F 2002/5006;
(Continued)

(56) References Cited

U.S. PATENT DOCUMENTS 8,597,369 B2    12/2013   Hansen et al.
9,549,827 B2    1/2017    Hansen et al.
(Continued)

FOREIGN PATENT DOCUMENTS

EP        1494626 B1 * 11/2006  ............. A61B 5/112
FR        1565589 A   *   5/1969  ............... A61F 2/68

OTHER PUBLICATIONS

FR1565589A Translation (Year: 1969).*

*Primary Examiner* — Christie Bahena
(74) *Attorney, Agent, or Firm* — Foley & Lardner LLP

(57) ABSTRACT

Technology is described to provide a foot and ankle prosthesis for individuals with lower limb loss. This technology is able to store and release energy and individuals or patients who are using the foot/ankle prosthesis may be able to expend less energy when walking. The system includes a hydraulic damper attached to dynamic energy storing spring elements. The axis of rotation of the system can be near to that of an intact human ankle, providing biomimetic function. The system can utilize spring elements based on the vertical displacement of the center of pressure of an intact normal foot. A hydraulic system can provide user adjustable heel height and adaptation to inclines. The dorsiflexion and plantar flexion resistances can be independently adjusted manually or electrically. In addition, the system can be automatically locked in dorsiflexion when loaded and unlock when unloaded.

19 Claims, 2 Drawing Sheets

(51) Int. Cl.
*A61F 2/76* (2006.01)
*A61F 2/50* (2006.01)
*A61F 2/68* (2006.01)

(52) U.S. Cl.
CPC ............. *A61F 2002/5006* (2013.01); *A61F 2002/5072* (2013.01); *A61F 2002/5079* (2013.01); *A61F 2002/6642* (2013.01); *A61F 2002/6854* (2013.01)

(58) Field of Classification Search
CPC ...... A61F 2002/5079; A61F 2002/6642; A61F 2002/6854
See application file for complete search history.

(56) References Cited

U.S. PATENT DOCUMENTS

| | | | |
|---|---|---|---|
| 10,105,243 B2 | 10/2018 | Hansen et al. | |
| 10,376,388 B2 | 8/2019 | Hansen et al. | |
| 2007/0010772 A1* | 1/2007 | Ryan | A61F 5/0123 602/26 |
| 2015/0066154 A1* | 3/2015 | Palmer, III | A61F 2/70 623/24 |
| 2019/0269529 A1* | 9/2019 | Arabian | A61F 2/6607 |

* cited by examiner

PROSTHETIC FOOT/ANKLE SYSTEM WITH AUTOMATIC ALIGNMENT

GOVERNMENT LICENSE RIGHTS

This invention was created in the performance of a Cooperative Research and Development Agreement with the Department of Veterans Affairs, an agency of the U.S. Government, which has certain rights in this invention.

BACKGROUND

Prostheses (or prosthetics) are artificial devices that replace body parts (e.g., fingers, hands, arms, legs, feet, toes, etc). Generally, prostheses may be used to replace body parts lost by injury, disease or missing from birth.

In one example, an intact human foot, connected to the ankle, travels through stance and swing phases of a gait cycle during each stride of motion, whether the motion involves walking, jogging, or running. By adjusting the stiffness and damping characteristics of a prosthetic foot and ankle mechanism, the springiness of the intact natural human foot and the corresponding natural human joints may be mimicked, thereby optimizing the prosthesis for the desired motion of the wearer. However, the characteristics that are desired to store and release energy appropriately for walking tend to oppose those best suited to fast walking and running.

DETAILED DESCRIPTION

Figure 1:
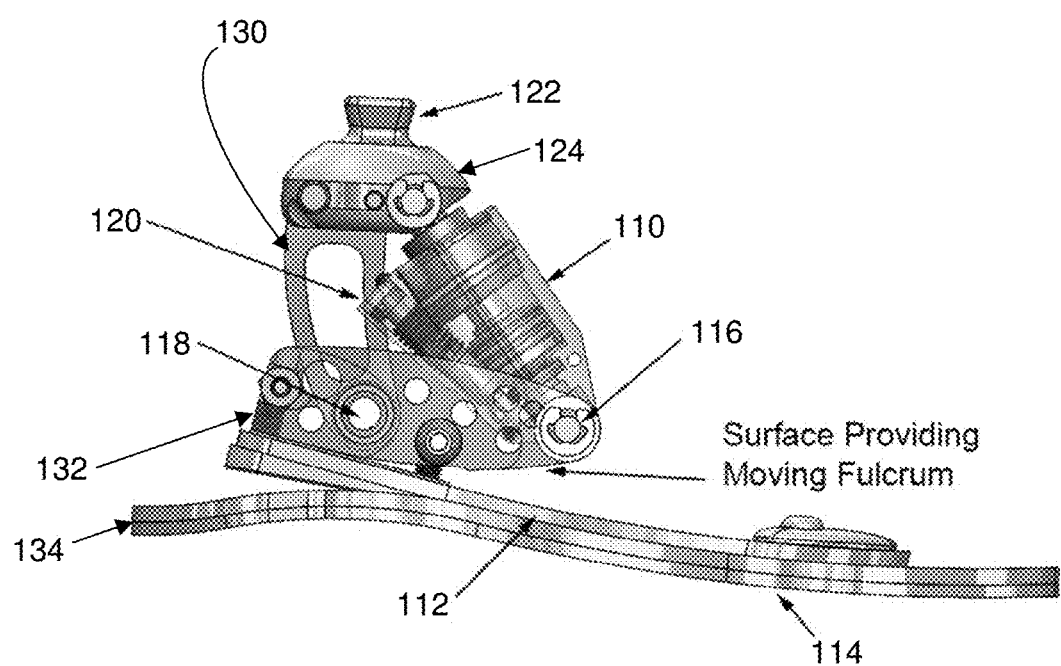
FIG. 1 illustrates an example of a prosthetic foot and ankle system that uses a linear hydraulic cylinder and rigid mounting for the energy storing spring elements.

Reference will now be made to the examples illustrated in the drawings, and specific language will be used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure are to be considered within the scope of the description.

A technology is described that involves a foot and/or ankle prosthesis for individuals with lower limb loss. This technology is able to store and release energy, and individuals or patients who are using the foot and/or ankle prosthesis are able to expend less energy when walking or running using this prosthetic device. The biomimetic prosthetic foot/ankle described herein provides example configurations that may improve the use of prosthetic ankles and feet for individuals using a prosthetic limb.

The device or system can include a prosthetic foot/ankle system with a linear hydraulic damper that is attached via a revolute joint to dynamic energy storing spring elements. The axis of rotation of the system or prosthetic ankle can be at an estimated position of an intact human ankle, providing biomimetic function. In one configuration, a mounting pyramid can allow for user alignment with a remnant limb.

The system or device can utilize spring elements that are curved to provide vertical displacement of the center of pressure as in an intact normal foot. For example, a curved surface on the energy storing sole plate can provide a fulcrum for the energy storing sole plate and main spring that produces a biomimetic force on a remnant limb. The system can further provide user adjustable heel height using a system to provide user adjustable heel height and adaptation to inclines. For example, the system can provide a user or amputee with an adjustable heel height using an adjustable sliding yoke. In addition, the system can be automatically locked in dorsiflexion when loaded by using mechanical assemblies, electrical systems or a combination of mechanical and electrical systems for locking purposes.

The system can have an adjustable stiffness toe-lift spring to lift the toe of the foot/ankle system rapidly after toe-off to reduce stumbling and hip hiking. The system can allow both dorsiflexion and plantar flexion resistance independently to vary heel strike hydraulic shock absorption and avoid foot slap at the foot flat position. This adjustment of dorsiflexion and plantar flexion resistance can be performed either by the user using manual hydraulic valves or by a microcontroller controlling electric hydraulic valves which affect the hydraulic shock absorption.

FIG. 1 shows elements of an example embodiment of the prosthetic foot/ankle system. The main housing or foot housing (not shown) can contain a linear hydraulic damper 110 that may be in a linear hydraulic cylinder mounted or indirectly attached to the energy storing spring elements (e.g., main spring element 112 and energy storing sole plate 114) via a front pivoting revolute joint 116 or cylinder front pivot and the main revolute joint 118 about which the foot pivots. The main revolute joint 118 may be located at a position that approximates or is close to an estimated or measured axis of rotation of the intact ankle. Manual adjustment valves or electric adjustment valves 120 may also be provided to adjust the dorsiflexion and plantar flexion resistance.

The energy storing spring elements 112, 114 may include an energy storing sole plate 114 that is a leaf spring. Another energy storing spring element may be a main spring 112 that is also a spring element. The vertical stiffness of the energy storing sole plate 114 and/or the main spring 112 are based on biomimetic stiffness of an intact foot. In one configuration, the main spring 112 may be an adjustable stiffness toe-lift spring to lift the toe after toe-off to reduce stumbling and hip hiking.

A pyramid 122 may attach to the housing through a coupling member or attachment yoke 124 which is connected to the linear hydraulic damper 110. As the pyramid 122 moves, the piston within the linear hydraulic damper 110 can displace hydraulic fluid. The resistances to hydraulic flow in the plantar and dorsiflexion flow directions may be controlled by the two independent manual adjustment valves and/or electric adjustment valves 120. Alternatively, the pyramid 122 may attach directly to a foot support 130 or foot post.

The orientation of the hydraulic damper 110 and the position of the main revolute joint 118 may also improve the functionality of the prosthetic foot/ankle system. This is because the position of the main revolute joint 118 is located with respect to the remnant limb to approximate the intact human foot/ankle. An individual amputee can ambulate (i.e., walk) with a more symmetric gait using this technology because the position of the main revolute joint can be located to estimate or be similar to (e.g., match) that of the primary axis of rotation of an intact ankle. The foot support 130 or forked support and base linkage 132 may also enable the main revolute joint 118 to be located at a position with respect to the remnant limb to approximate or mimic the intact human foot/ankle. In one example, the foot support may be foot support 130 (e.g., a foot post) with one, two, three or more support columns, posts or forks.

The horizontal distance from the heel 134 to the main revolute joint 118 may be approximately one-third of the length of the foot. The vertical distance from the ground to the main revolute joint may be approximately one-eighth the length of the foot.

The determination of the stiffness of the spring elements may be based on the vertical displacement of the center of pressure of an intact normal foot. The center of pressure is the position of maximum pressure on the bottom of the foot during normal walking. This center of pressure moves from the heel at heel-strike to the toe at toe-off. The shape and stiffness of the spring elements of foot/ankle system are designed in such a way that the center of pressure progresses from heel to toe in a way that approximates or mimics the intact foot. Furthermore, the stiffness of the foot can be designed such that the vertical deflection of the spring elements approximates the vertical deflection of an intact foot at the center of pressure as the pressure progresses from heel to toe.

The pyramid 122 may be oriented such that the overall system is able to rotate through a defined number of degrees of hydraulic motion (e.g., 15 degrees) in the heel to toe direction.

The foot/ankle system may automatically adjust for heel height and inclines by means a hydraulic mechanism that locks the hydraulic cylinder to dorsiflexion after heel strike and before foot-flat. For example, the hydraulic cylinder locking mechanism or cylinder lock may be a weighted valve mechanism that locks the hydraulic cylinder after heel strike. Alternatively, the hydraulic cylinder locking mechanism may be an electronic timing system that locks after heel strike at the appropriate time. In another configuration, the hydraulic cylinder locking mechanism may be based on accelerometers, orientation sensors, pressure sensors and/or other electronic sensors that provide feedback on when to lock and unlock the hydraulic cylinder.

The foot/ankle system can adapt to slopes and uneven surfaces. This adaptation is achieved by allowing the ankle to plantar flex when an individual using the foot puts weight on the prosthesis. At a certain point in the gait, a hydraulic mechanism may lock the ankle in dorsiflexion. Hydraulic resistance to plantar flexion can be adjusted by means of a manually or electrically adjustable hydraulic valve. Adjusting the plantar flexion hydraulic resistance allows the user to adjust the amount of hydraulic shock absorption at heel strike. Such shock absorption may also be provided by the foot/ankle toe-lift spring. Both energy-dissipating hydraulic impedance and the energy-storing spring elements resist plantar flexion. Both plantar flexion hydraulic impedance and the spring elements impedances can be adjustable such that the system can exhibit the desired amount of shock absorption.

Figure 2:
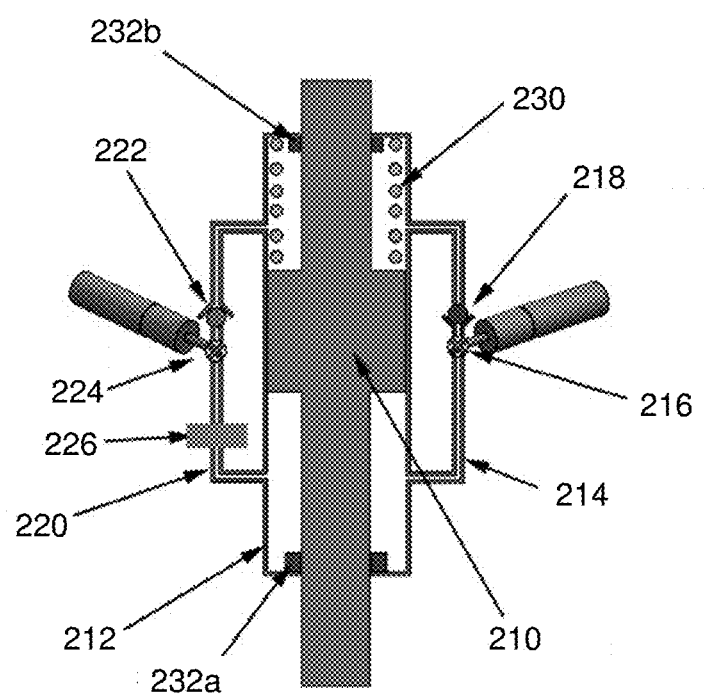
FIG. 2 illustrates a schematic of an example of a hydraulic prosthetic foot and ankle system that automatically aligns for varying heel heights and inclines.

FIG. 2 shows a schematic of an example configuration of the foot/ankle system which enables locking of the hydraulic cylinder 212. Seals 232a, 232b may be used to retain fluid within the hydraulic cylinder 212. When the ankle rotates, the linear hydraulic piston 210 can move within the hydraulic cylinder 212. When the ankle plantar flexes, the linear hydraulic piston 210 forces fluid through the plantar flexion hydraulic pathway 214 (e.g., tubing, channels, etc.) with its respective plantar flexion check valve 218 and plantar flexion resistance adjustment valve 216.

When the ankle is dorsi-flexed, the linear hydraulic piston 210 in the hydraulic cylinder 212 can force fluid through the dorsiflexion hydraulic pathway 220 with its respective dorsiflexion check valve 222 and dorsiflexion resistance adjustment valve 224. A check valve may be a flapper check valve located near the linear hydraulic piston 210 to minimize resistance and facilitate toe-lift during the swing phase of the gait cycle. In addition, the dorsiflexion hydraulic pathway 220 may include a hydraulic cylinder locking mechanism 226 that automatically locks after heel strike and before foot flat. This hydraulic cylinder locking mechanism 226 may unlock the ankle to dorsiflexion after toe-off due to the shift in the pressure differential across the hydraulic piston. The unlocked dorsiflexion may allow a toe-lift spring to lift the toe during swing phase, providing ground clearance. The hydraulic cylinder 212 may also contain an optional internal toe lift spring 230 that is within the hydraulic cylinder 212. The structure and operations that are described with respect to a linear hydraulic piston and cylinder may also be applied to a rotary hydraulic configuration.

Reference was made to the examples illustrated in the drawings, and specific language was used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure, are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology can be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements can be devised without departing from the spirit and scope of the described technology.

The invention claimed is:

1. A device to control movement of a prosthetic foot and ankle, comprising:
   a foot support to provide a portion of the prosthetic foot;
   a revolute joint attached to the foot support;
   a hydraulic damper attached to the foot support,
   an energy storing spring attached to the revolute joint and the energy storing spring is attached to the hydraulic damper to provide resistive communication with the hydraulic damper; and
   a hydraulic cylinder lock that is a weighted valve mechanism for the hydraulic damper to lock the revolute joint for dorsiflexion between heel strike and foot flat and to unlock the ankle for dorsiflexion upon unloading of a toe to allow automatic dorsiflexion by a toe-lift spring.

2. The device as in claim 1, wherein the hydraulic damper is a linear hydraulic damper.

3. The device as in claim 1, wherein the energy storing spring is an energy storing sole plate attached to a housing of the hydraulic damper through the revolute joint and a base linkage.

4. The device as in claim 3, wherein the energy storing sole plate is a leaf spring.

5. The device as in claim 3, further comprising a curved surface on the energy storing sole plate that provides a fulcrum for the energy storing sole plate and main spring that produces a biomimetic force on a remnant limb.

6. The device as in claim 1, wherein a vertical stiffness of an energy storing sole plate and a main spring are based on a selected stiffness.

7. The device as in claim 1, wherein the revolute joint is configured to have an axis of rotation of the revolute joint is at a selected position.

8. The device as in claim 1, further comprising a mounting pyramid attached to the foot support to enable user alignment with a remnant limb of an amputee.

9. The device as in claim 1, further comprising an adjustable stiffness toe-lift spring that is a main spring to lift the toe after toe-off to reduce stumbling and hip hiking.

10. The device as in claim 1, wherein the hydraulic cylinder lock is located with a hydraulic piston.

11. The device as in claim 1, wherein a flapper check valve is located with a hydraulic piston of the hydraulic damper to minimize resistance and facilitate toe-lift during a swing phase of a gait cycle.

12. The device as in claim 1, further comprising an accessible manual hydraulic valve to allow a user to easily adjust dorsiflexion resistance and plantar flexion resistance independently in order to vary heel strike hydraulic shock absorption and avoid foot slap at foot flat position.

13. The device as in claim 1, further comprising an electric hydraulic valve to enable adjustment of dorsiflexion resistance and plantar flexion resistance independently in order to vary heel strike hydraulic shock absorption and avoid foot slap at foot flat position.

14. A device to control movement of a prosthetic foot and ankle, comprising:
   a foot support for the prosthetic foot;
   an energy storing sole plate;
   a main spring attached to the energy storing sole plate;
   a revolute joint coupled to the main spring, wherein the energy storing sole plate is attached to the foot support through the revolute joint and a base linkage;
   a linear hydraulic damper associated with the energy storing sole plate and main spring and attached to the foot support, wherein the linear hydraulic damper has a weighted valve mechanism that either locks the ankle for dorsiflexion between heel strike and foot flat to automatically align the ankle to accommodate for heel height and changes in incline or unlocks the ankle for dorsiflexion upon unloading of a toe to allow automatic dorsiflexion by a toe-lift spring; and
   wherein the energy storing sole plate is in resistive communication with the linear hydraulic damper through the base linkage attached to the linear hydraulic damper.

15. The device as in claim 14, wherein the energy storing sole plate is a leaf spring.

16. The device as in claim 14, wherein the revolute joint is configured to have an axis of rotation of the revolute joint is at a selected location.

17. The device as in claim 14, further comprising a manual hydraulic valve or electric hydraulic valve to allow a user to adjust both dorsiflexion resistance and plantar flexion resistance independently in order to vary heel strike hydraulic shock absorption and avoid foot slap at foot flat position.

18. A device to control movement of a prosthetic foot and ankle, comprising:
   a foot support for the prosthetic foot;
   a mounting pyramid attached to the foot support to enable user alignment with a remnant limb of an amputee;
   a revolute joint attached to the foot support to provide an estimated ankle joint for the prosthetic foot;
   a main spring coupled to the revolute joint;
   an energy storing sole plate attached to the main spring;
   a linear hydraulic damper attached to the foot support, wherein a linear hydraulic damper lock that is a weighted valve mechanism locks the ankle for dorsiflexion between heel strike and foot flat to automatically align the ankle to accommodate for heel height and changes in incline and unlocks the ankle for dorsiflexion upon unloading of a toe to allow automatic dorsiflexion by the main spring; and
   wherein the energy storing sole plate is in resistive communication with the linear hydraulic damper through the main spring and a base linkage.

19. The device as in claim 18, further comprising a manual hydraulic valve or electric hydraulic valve to allow a user to easily adjust both dorsiflexion resistance and plantar flexion resistance independently in order to vary heel strike hydraulic shock absorption and avoid foot slap at foot flat position.

* * * * *